United States Patent

Solladie et al.

Patent Number: 5,296,505
Date of Patent: Mar. 22, 1994

[54] COMPOSITIONS OF RETINOIDS SUBSTITUTED WITH A DITHIANE RING, THEIR USE, AND PROCESS FOR PREPARING THE COMPOUNDS

[75] Inventors: Guy Solladie, Strasbourg; Valérie Berl, Mulhouse; Jean Maignan, Tremblay-Les-Gonesse, all of France

[73] Assignee: L'Oreal, Paris, France

[21] Appl. No.: 897,763

[22] Filed: Jun. 12, 1992

[30] Foreign Application Priority Data

Jun. 14, 1991 [FR] France ................. 91 07292

[51] Int. Cl.$^5$ ................. A61K 31/385; C07D 339/08
[52] U.S. Cl. ................. 514/436; 549/20; 549/21; 424/70
[58] Field of Search ............ 549/20, 21; 568/477; 514/436, 703; 424/70

[56] References Cited

U.S. PATENT DOCUMENTS 5,093,360 3/1992 Yu et al. ................. 514/703

FOREIGN PATENT DOCUMENTS 0292350 11/1988 European Pat. Off. .
0391033 10/1990 European Pat. Off. .
2028818 3/1980 United Kingdom .

OTHER PUBLICATIONS

Bhatt: "Vitamin A Derivatives", Chemical Abstracts, vol. 92, No. 9, 1980, Abstract No. 76738S.
T. Greene, "Protective Groups in Organic Synthesis," pp. 134–138 John Wiley & Sons, New York (1981).

Primary Examiner—Richard L. Raymond
Attorney, Agent, or Firm—Cushman, Darby & Cushman

[57] ABSTRACT

The invention relates to a stereospecific derivative of formula:

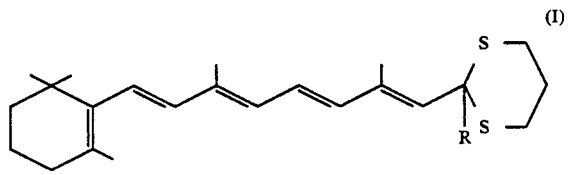

in which R is hydrogen or a $C_1$–$C_4$ thioalkyl. The invention also relates to the use of these compounds for the manufacture of stereospecific retinal or retinoic acid, as well as to a process for preparing the retinoids of formula (I). The invention finally relates to a cosmetic or pharmaceutcial composition which contains at least one compound of formula (I) in a suitable vehicle; the pharmaceutical composition according to the invention may be used for treating dermatological, rheumatic, respiratory or ophthalmological conditions.

5 Claims, No Drawings

COMPOSITIONS OF RETINOIDS SUBSTITUTED WITH A DITHIANE RING, THEIR USE, AND PROCESS FOR PREPARING THE COMPOUNDS

The present invention relates to retinoid derivatives substituted with a dithiane ring, to a process for preparing them, to their use as a starting point for hydrolysis and to their use in human and veterinary medicine and in cosmetics, in the form of compositions.

The retinoid family comprises natural compounds, in particular vitamin A or retinol, retinal and retinoic acid, and a number of derivatives obtained synthetically.

Retinoids are, in a known manner, compounds used for the cosmetic or pharmaceutical treatment of skin conditions associated with disturbances of epidermal differentiation, such as psoriasis or acne. It is very important to have control over the stereochemistry of the various reactions for the synthesis of retinoids, so as to obtain retinoids having a particular stereospecificity and not retinoids in the form of a mixture of different stereoisomers. In effect, the mode of use of retinoids can differ according to their stereochemical form. For example, clinically, all-trans-retinoic acid is used topically and 13-cis retinoic acid is used systemically.

The present invention relates to sulphur-containing retinoic compounds, prepared in a particular stereochemical form, all-trans or 13-cis, capable on hydrolysis of being converted to retinal or retinoic acid having the same stereospecific form, and to a manufacturing process enabling these compounds to be prepared in a particular stereochemical form from a starting compound, termed "synthon", of corresponding stereospecific form.

The subject of the present invention is hence a stereospecific retinoic compound of formula:

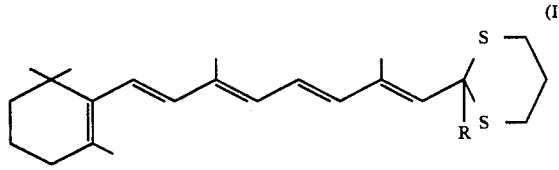

(I)

in which formula R is H or a $C_1$–$C_4$ thioalkyl radical.

In the present text and by convention, the trans position of the dithiane ring is represented by placing the axis of symmetry of this ring pointing obliquely upwards, and the cis position by orienting the said axis downwards. When this axis is shown horizontal, the formula denotes the cis stereospecific form or the trans stereospecific form without discrimination.

The present invention relates, more especially, to the all-trans-retinal thioacetal of formula:

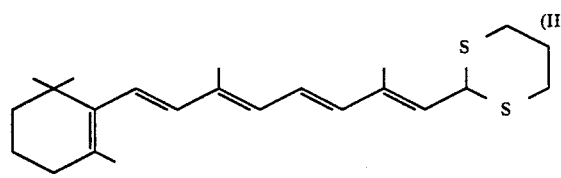

(II)

to the 13-cis-retinal thioacetal of formula:

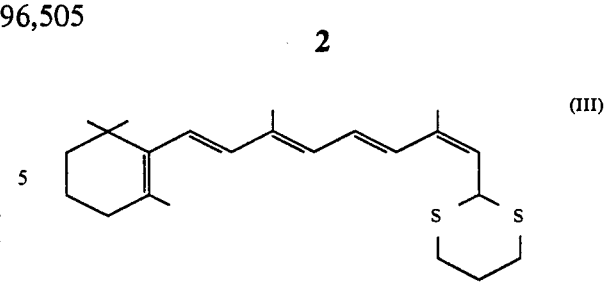

(III)

and to the retinoic acid trans-(ortho thioester) of formula:

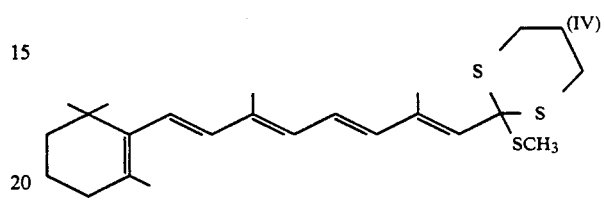

(IV)

It was checked that these products have a retinoic action, as their structure would lead one to suppose. Moreover, on hydrolysis, the compounds of formula (I) give retinal or retinoic acid in the stereospecific form corresponding to that of the formula (II) and (III) give all-trans-retinal and 13-cis-retinal and the compound of formula (IV) retinoic acid in trans form, respectively.

The subject of the invention is hence also the use of the compounds of formula (I) for obtaining on hydrolysis a stereospecific retinal or retinoic acid.

The compounds of formula (I) are prepared from diols having the corresponding stereospecificity, of formula:

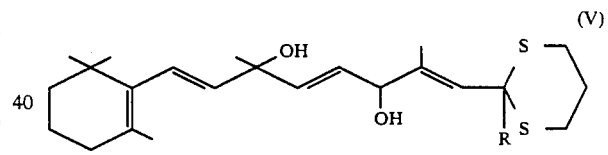

(V)

where R has the same meaning as above, by reduction using "low-valency" titanium so as to eliminate the two hydroxyl groups and obtain a fourth double bond. "Low-valency" titanium is obtained, in a known manner, by reduction of $TiCl_3$ or $TiCl_4$ with a metal such as magnesium, potassium, sodium, lithium, the zinc/copper system or a lithium aluminium hydride. A mixture of $TiCl_3$ and $LiAlH_4$ is preferably used. In FR-A-2,615,509, a process is described for the reduction of a triene diol to a retinoic compound containing four conjugated ethylenic double bonds. According to the present invention, it was found that, in the case of the diols of formula (V) above, reduction using "low-valency" titanium enabled the stereospecificity to be preserved. In other words, using, for example, an all-trans compound of formula (V), an all-trans retinoid is obtained.

The diols of formula (V) are prepared by reacting a stereospecific dithianepropenal of formula:

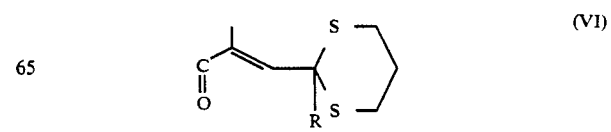

(VI)

where R has the same meaning as above, with ethynyl-β-ionol of formula:

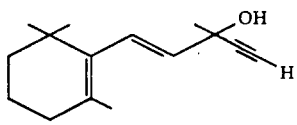 (VII)

by a Grignard reaction in the presence of an organomagnesium compound, so as to obtain the acetylenic compound of formula:

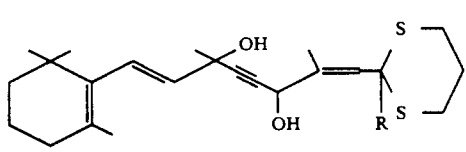 (VIII)

where R has the same meaning as above, followed by hydrogenation of the compound of formula (VIII) to obtain the diol of formula (V). The hydrogenation is preferably performed using lithium aluminium hydride.

During these various reactions, the stereospecificity of the dithiane ring with respect to the closest double bond is not altered.

The subject of the invention is hence also the process for preparing the compounds of formula (I) from the compounds of formula (VI) by the various steps defined above.

Some of the dithianepropenals of formula (VI) used are known. This applies, in particular, to the trans-dithianepropenal of formula:

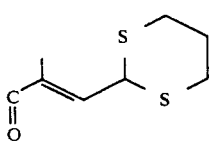 (VIa)

which is described in T. SAKO, K. HANAYAMA and T. FUJISAWA Tetrahedron Letters, 29, 2197 (1988) and K. RUSTEMEIER and E. BREITMAIER Chem. Ber, 115, 3898 (1982). Other dithianepropenals are new products whose synthesis is described in detail in a patent application filed by the Applicant on the same date as the present application and the content of which is to be considered as incorporated in the present text by reference; this applies, for example, to the cis-dithianepropenal of formula:

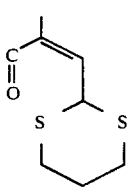 (VIb)

and to the trans-(ortho thioester) of formula:

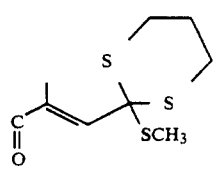 (VIc)

The new compounds of formula (I) also find application in the topical and systemic treatment of dermatological conditions linked to a disorder of keratinisation (differentiation/proliferation) and dermatological or other conditions having inflammatory and/or immunoallergic components, and in degenerative diseases of connective tissue, and possess antitumour activity. In addition, these compounds may be used in the treatment of atopy, either cutaneous or respiratory, and rheumatoid psoriasis. They also find application in the ophthalmological field, in particular in the treatment of corneopathies.

The compounds according to the invention are especially appropriate in the following fields of treatment:

1) for treating dermatological conditions linked to a disorder of keratinisation involving differentiation and proliferation, in particular for treating acne vulgaris, comedonic or polynorphic acne, nodulocystic acne, acne conglobata, senile acne and secondary acnes such as solar, drug or occupational acne;

2) for treating other types of disorders of keratinisation, especially ichthyoses, ichthyosiform conditions, Darier's disease, palmoplantar keratoderma, leucoplakia and leucoplakiform conditions, and lichen;

3) for treating other dermatological conditions linked to a disorder of keratinisation with an inflammatory and/or immunoallergic component, and in particular all forms of psoriasis, either cutaneous, mucosal or ungual; and even psoriatic rheumatism, or alternatively cutaneous atopy such as eczema or respiratory atopy; and also for treating some inflammatory conditions not involving a disorder of keratinisation;

4) for treating all dermal or epidermal proliferations, either benign or of viral origin, such as common warts, flat warts and epidermodysplasia verruciformis, it also being possible for the proliferations to be induced by ultraviolet light, in particular in the case of basal cell and prickle cell epithelioma;

5) for treating other dermatological disorders such as vesicular dermatoses and collagen diseases;

6) for treating certain ophthalmological disorders, in particular corneopathies;

7) for correcting and combating skin ageing, either light-induced or due to the passage of time;

8) for preventing or treating the stigmata of epidermal and/or dermal atrophy induced by local or systemic corticosteroids, or any other form of cutaneous atrophy;

9) for promoting cicatrisation;

10) for combating disorders of sebaceous function, such as seborrhoea associated with acne or simple seborrhoea;

11) for treating cancerous or precancerous conditions, especially those of skin;

12) for treating inflammatory conditions such as arthritis.

The subject of the present invention is hence also a pharmaceutical composition containing at least one compound of formula (I) as defined above in a vehicle suitable for enteral, parenteral, topical or ocular administration, as well as the use of such a composition for the treatment of the abovementioned conditions. The compounds of formula (I) are generally administered at a daily dosage of approximately 0.01 mg to approximately 100 mg/kg of body weight, in 1 to 3 doses.

For enteral administration, the pharmaceutical compositions of the invention can take the form of tablets, of hard gelatin capsules, of dragees, of syrups, of suspensions, of solutions, of powders, of granules, of emulsions, of microspheres or nanospheres or other lipid or polymer vesicles permitting a controlled release.

For parenteral administration, the pharmaceutical compositions according to the invention can take the form of solutions or suspensions for perfusion or injection.

In the case of topical administration, the pharmaceutical compositions of the invention are intended for treatment of the skin and the mucosae, and take the form of ointments, of creams, of milks, of salves, of powders, of impregnated pads, of solutions, of gels, of sprays, of lotions or of suspensions; they can also take the form of microspheres or nanospheres or of lipid or polymer vesicles or of polymer "patches" or of hydrogels permitting a controlled release; they can take either anhydrous form or aqueous form, depending on the clinical indication.

For ocular administration, the pharmaceutical compositions of the invention are mainly eye-washes.

The pharmaceutical compositions of the invention contain at least one compound of formula (I) as defined above, preferably at a concentration of between 0.0001 and approximately 5% by weight relative to the total weight of the composition.

The compounds of formula (I) also find application in the cosmetic field, especially in body and hair hygiene, and in particular for treating skin having a tendency to develop acne, for inducing hair regrowth and combating hair loss, for combating a greasy appearance of the skin or the hair, in protection against the deleterious effects of sunlight or in the treatment of physiologically dry skin.

The subject of the present invention is hence, finally, a cosmetic composition containing at least one compound of formula (I) in a suitable cosmetic vehicle, this composition taking, in particular, the form of a cream, of a milk, of a lotion, of a gel, of microspheres or nanospheres or of lipid or polymer vehicles, of a soap or of a shampoo. The concentration of compound(s) of formula (I) in these cosmetic compositions is preferably between 0.0001 and approximately 3% by weight relative to the total weight of the composition.

The pharmaceutical and cosmetic compositions according to the invention can contain inert additives or pharmacodynamically or cosmetically active additives.

The examples given below, purely by way of illustration and without implied limitation, will enable a better understanding of the invention to be gained.

EXAMPLE 1

Preparation of the Retinoid of Formula (II)

A) Preparation of the Starting Synthon Consisting of the Dithianepropenal of Formula

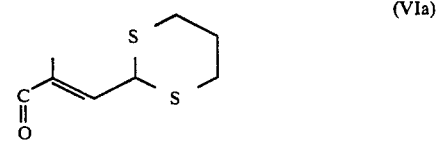
(VIa)

The preparation is carried out according to the scheme given below.

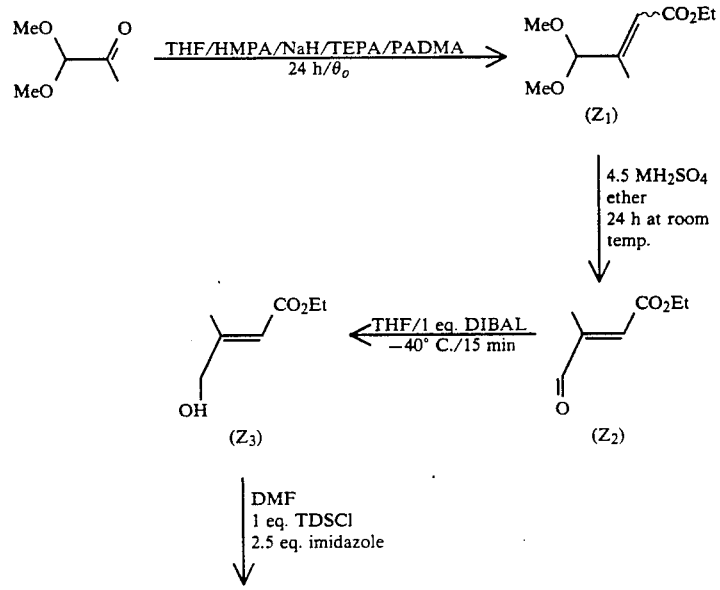

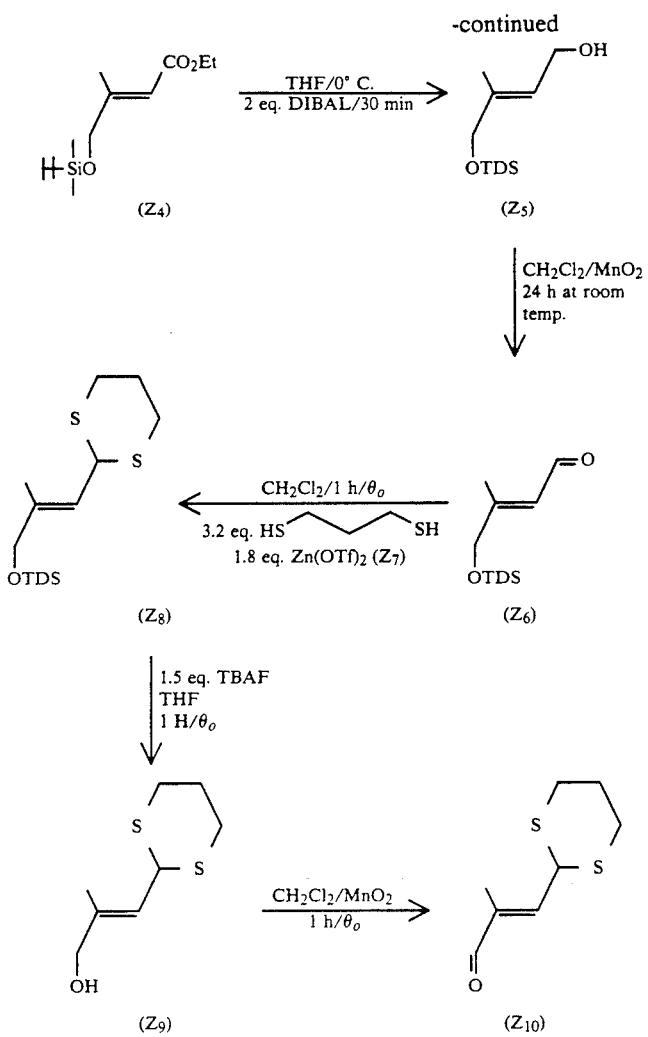

In this scheme, the intermediate compounds are designated by the references ($Z_i$), i being an integer ranging from 1 to 10; $\Theta_0$ denotes room temperature. The total yield of the preparation is 49%.

1st step: Preparation of ethyl (E/Z)-4-oxo-3-methyl-2-butenoate dimethyl acetal ($Z_1$) of formula:

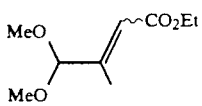

with Et=ethyl

In a round-bottomed flask, sodium hydride (15.3 g-0.64 mol) is suspended in anhydrous tetrahydrofuran (THF) (100 ml) under argon. After the medium is cooled to 0° C., a mixture of hexamethylphosphoramide (HMPA) (10 ml) and triethyl phosphonoacetate (TEPA) (142 g-0.64 mol) is added dropwise and with stirring. After one hour, the solution has assumed a brownish tint, and one equivalent of pyruvaldehyde dimethyl acetal (PADMA) (72.2 g-0.64 mol) is added slowly. Stirring is maintained for 24 hours at room temperature. During the reaction, a brown gum deposits at the bottom of the reaction flask. It is dissolved by adding water (150 ml). The medium is then extracted with ether (2×100 ml). The combined organic phases are washed with saturated NaCl solution (2×150 ml), dried over $Na_2SO_4$ and then evaporated. 114 g of a slightly yellow liquid, consisting of a mixture of the E/Z isomers in the ratio 6:1, are obtained.

The yield is 95%.

The characteristics are as follows:
a) Thin-layer chromatography (TLC) on silica gel: (hexane/ethyl acetate, 70:30) Rf≈0.66
b) M=188.23
c) The structure was confirmed by a ($^1$H) NMR and ($^{13}$C) NMR nuclear magnetic resonance study (200 MHz) ($CDCl_3$) and by studying the infrared (IR) spectrum ($CCl_4$).

2nd step: Preparation of ethyl γ-oxosenecioate in trans form ($Z_2$), of formula:

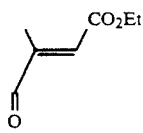

with Et=ethyl

A 1:1 mixture of 4.5M sulphuric acid and ether (400 ml) is cooled using an ice bath. The acetal ($Z_1$) (mixture of E/Z isomers) is added dropwise and with stirring (20 g-106 mmol). After 24 hours, the medium is extracted with ether (3×150 ml). After the organic phases are washed with saturated $NaHCO_3$ solution (250 ml), with water (150 ml) and finally with saturated NaCl solution (200 ml) and then dried over sodium sulphate, the solvent is evaporated off. 11.75 g of a very pale yellow liquid are obtained.

The yield is 78%.

The characteristics of the product are as follows:
a) Thin-layer chromatography (hexane/ethyl acetate, 70:30) $Rf \approx 0.66$
b) Molecular mass M=142.16
c) The structure was confirmed by a ($^1H$) NMR study (200 MHz) ($CDCl_3$) and by studying the infrared spectrum ($CCl_4$).

3rd step: Preparation of ethyl trans-≡-hydroxy-senecioate ($Z_3$) of formula:

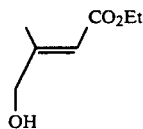

with Et=ethyl

The aldehyde ($Z_2$) (10 g–0.07 mol) is dissolved in anhydrous tetrahydrofuran (THF) (300 ml) under argon. After the medium is cooled to −40° C., one equivalent of diisobutylaluminium hydride (DIBAL) (70.3 ml of 1M solution in toluene) is rapidly added dropwise. After 15 minutes at this temperature, the medium is hydrolysed by the slow addition of methanol (20 ml) followed by water (100 ml). As soon as the temperature has reached 0° C., 100 ml of ether are added, and 10% (by volume) hydrochloric acid is then added with vigorous stirring until two clear phases are obtained. The aqueous phase is extracted with ether (3×100 ml). The combined organic phases are washed with saturated NaCl solution (150 ml), dried over $Na_2SO_4$ and then concentrated. The crude reaction product is chromatographed on a silica column (eluent=hexane/ethyl acetate, 70:30). 8.75 g of a yellow liquid are obtained.

The yield is 86%.

The characteristics of the product are as follows:
a) Thin-layer chromatography (hexane/ethyl acetate, 70:30) $Rf \approx 0.27$
b) M=144.17
c) The structure was confirmed by ($^1H$ and $^{13}C$) NMR (200 MHz) ($CDCl_3$) and infrared (IR) spectrum.
d) Elemental analysis gives the following results:

| % | Calculated | Found |
|---|---|---|
| C | 58.32 | 58.60 |
| H | 8.39 | 8.63 |

4th step: Preparation of ethyl trans-(t-hexyldimethylsiloxy)senecioate ($Z_4$) of formula:

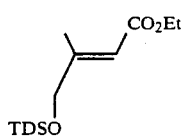

with TDS=t-hexyldimethylsilyl and Et=ethyl.

$MgSO_4$, flamed under vacuum (approximately 6 g) is added to the alcohol ($Z_3$) (8.7 g–0.06 mol) dissolved in dimethylformamide (DMF) distilled on molecular sieve (160 ml) and under argon. The medium is stirred for 10 minutes at room temperature, and then one equivalent of t-hexyldimethylsilyl chloride (11.85 ml) followed by 2.5 equivalents of imidazole (10.27 g) are added. After 0.5 h of stirring at room temperature, the reaction mixture is diluted with water (100 ml) and extracted with ether (4×100 ml). The combined organic phases are washed with saturated $NH_4Cl$ solution (2×100 ml) and saturated NaCl solution (100 ml), dried over $Na_2SO_4$ and then concentrated. 15.45 g of a pale yellow liquid are obtained, which liquid may be purified by chromatography on a silica column (eluent=hexane/ether, 95:5).

The yield is 90%.

The characteristics of the product are as follows:
a) TLC (hexane/ethyl acetate, 70:30) $Rf \approx 0.85$
b) M=286.49
c) The structure was confirmed by ($^1H$ and $^{13}C$) NMR (200MHz) ($CDCl_3$) and by IR.
d) Elemental analysis gives the following results:

| % | Calculated | Found |
|---|---|---|
| C | 62.89 | 62.90 |
| H | 10.55 | 10.69 |

5th step: Preparation of trans-(t-hexyldimethylsiloxy)-seneciol ($Z_5$) of formula:

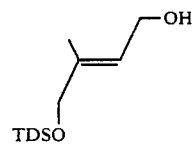

with TDS=t-hexyldimethylsilyl

The ester ($Z_4$) (10 g–0.035 mol) is dissolved in anhydrous tetrahydrofuran (THF) (200 ml) under argon. After the medium is cooled to 0° C., 2.2 equivalents of diisobutylaluminium hydride (DIBAL) (77 ml of 1M solution in toluene) are rapidly added dropwise. After 0.5 h, the reaction is complete and the medium is hydrolysed by the slow addition of methanol (3.7 ml). The mixture is poured into a mixture of ethyl acetate (1500 ml) and saturated sodium tartrate solution (190 ml). Vigorous stirring of this medium for 1 h enables the gel which has formed to be "broken". The aqueous phase is then extracted with ethyl acetate (3×150 ml). The combined organic phases are washed with saturated NaCl solution (150 ml), dried over $Na_2SO_4$ and then concentrated. 8.55 g of product ($Z_5$) are obtained.

The characteristics of the product obtained are as follows:
a) TLC (hexane/ethyl acetate, 70:30) $Rf \approx 0.51$
b) M=244.46
c) The structure was confirmed by ($^1H$ and $^{13}C$) NMR (200MHz) ($CDCl_3$) and by IR.
d) Elemental analysis gives the following results:

| % | Calculated | Found |
|---|---|---|
| C | 63.88 | 64.01 |
| H | 11.54 | 11.75 |

6th step: Preparation of trans-(t-hexyldimethylsiloxy)-senecioaldehyde ($Z_6$) of formula:

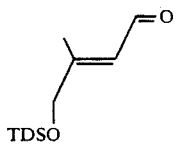

with TDS=t-hexyldimethylsilyl

The alcohol ($Z_5$) (7 g–0.0286 mol) is equivalents of manganese dioxide (12 g) are added to the medium with vigorous stirring. After 24 h at room temperature, the suspension is filtered through a thin layer of silica. The silica is washed copiously with ethyl acetate. The filtrate is concentrated under vacuum, avoiding heating. 6.94 g of a slightly volatile yellow liquid are recovered.

The characteristics of the product obtained are as follows:
a) TLC (hexane/ethyl acetate, 70:30) Rf≈0.73
b) M=242.44
c) The structure was confirmed by ($^1$H and $^{13}$C) NMR (200MHz) (CDCl$_3$) and by IR.
d) Elemental analysis gives the following results:

| % | Calculated | Found |
|---|---|---|
| C | 64.40 | 64.11 |
| H | 10.81 | 10.97 |

7th step: Preparation of zinc triflate ($Z_7$): Zn(OTf)$_2$.

One equivalent of zinc carbonate (17.4 g–0.139 mol) is dissolved in dry methanol (250 ml). Using a dropping funnel, 1.4 equivalents of triflic acid (50 g–0.195 mol) are slowly added dropwise. The reaction is exothermic and a vigorous evolution of CO$_2$ is observed. The medium is stirred for 20 minutes at room temperature and then 2 h under reflux. The methanol is then evaporated off. The residue is dried by heating for 2.5 h at 130° C. at 330 pascals. 50.4 g of a white powder are obtained (M=363.53).

8th step: Preparation of (E)-3-(1,3-dithian-2-yl)-2-methyl-(t-hexyldimethylsilyl)propenol ($Z_8$) of formula:

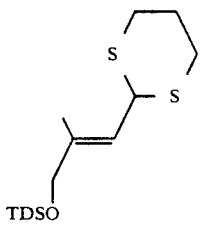

with TDS=t-hexyldimethylsilyl 3.2 equivalents of 1,3-propanedithiol (8.9 ml–0.088 mol) and 1.2 equivalents of Zn(OTf)$_2$ (12.05 g–0.033 mol) are dissolved in distilled CH$_2$Cl$_2$ (200 ml) under argon. After the medium is stirred for 15 minutes at room temperature, one equivalent of the aldehyde ($Z_6$) (6.7 g–0.0276 mol), dissolved in CH$_2$Cl$_2$ (20 ml), is rapidly added dropwise. Reaction is complete after 0.5 h and the medium is diluted by adding water (150 ml). The aqueous phase is extracted with a 1:1 hexane/ether mixture (3×150 ml). The combined organic phases are washed with 10% hydrochloric acid (150 ml) in order to "break" the emulsion which has formed, then with 0.5M caustic soda (3×200 ml), saturated NaHCO$_3$ solution (150 ml), water (2×150 ml) and finally saturated NaCl solution (150 ml). After drying over Na$_2$SO$_4$ and evaporation of the solvent, 8.73 g of a colourless oil are isolated.

The yield is 95%.

The characteristics of the product obtained are as follows:
a) TLC (hexane/ethyl acetate, 90:10) Rf≈0.58
b) M=332.65
c) The structure was confirmed by ($^1$H and $^{13}$C) NMR (200MHz) (CDCl$_3$) and by IR.
d) Elemental analysis gives the following results:

| % | Calculated | Found |
|---|---|---|
| C | 57.77 | 59.79 |
| H | 9.7 | 9.56 |

9th step: Preparation of (E)-3-(1,3-dithian-2-yl)-2-methylpropenol ($Z_9$) of formula:

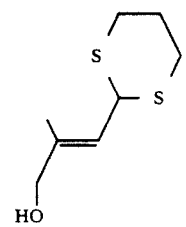

1.5 equivalents of tetrabutylammonium fluoride (38.3 ml of 1M solution in THF) are added to one equivalent of the silyl compound ($Z_8$) (8.5 g–0.0255 mol) dissolved in anhydrous tetrahydrofuran (THF) (80 ml) and under argon. The reaction medium is stirred for 1 h at room temperature and then passed through a thin layer of Celite. The reaction flask and the Celite are rinsed with ether. After concentration of the filtrate, 4.86 g of a pale yellow liquid are recovered.

The characteristics of the product obtained are as follows:
a) TLC (hexane/ethyl acetate, 70:30) Rf≈0.29
b) M=190.33
c) The structure was confirmed by ($^1$H and $^{13}$C) NMR (200MHz) (CDCl$_3$) and by IR.
d) Elemental analysis gives the following results:

| % | Calculated | Found |
|---|---|---|
| C | 50.49 | 50.52 |
| H | 7.41 | 7.57 |

10th step: Preparation of (E)-3-(1,3-dithian-2-yl)-2-methylpropenal ($Z_{10}$) of formula:

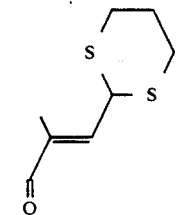

The alcohol ($Z_8$) (4.8 g–0.025 mol) is dissolved in distilled CH$_2$Cl$_2$ (150 ml) under argon. Approximately five equivalents of manganese dioxide (11 g) are added to the medium with vigorous stirring. After 4 h at room temperature, the suspension is filtered through a thin layer of silica. The silica is washed copiously with ethyl acetate. The filtrate is concentrated under vacuum. 4.24 g of beige crystals are The yield is 90%.

The characteristics of the product obtained are as follows:
a) TLC (hexane/ethyl acetate, 70:30) $Rf \approx 0.52$
b) Melting point m.p.$=38°-39°$ C.
c) $M=188.32$
d) The structure was confirmed by ($^1$H and $^{13}$C) NMR (200MHz) (CDCl$_3$) and by IR.
e) Elemental analysis gives the following results:

| % | Calculated | Found |
|---|---|---|
| C | 51.02 | 51.20 |
| H | 6.42 | 6.47 |

B) Preparation of the Retinoid of Formula (II)

The preparation is performed according to the following scheme

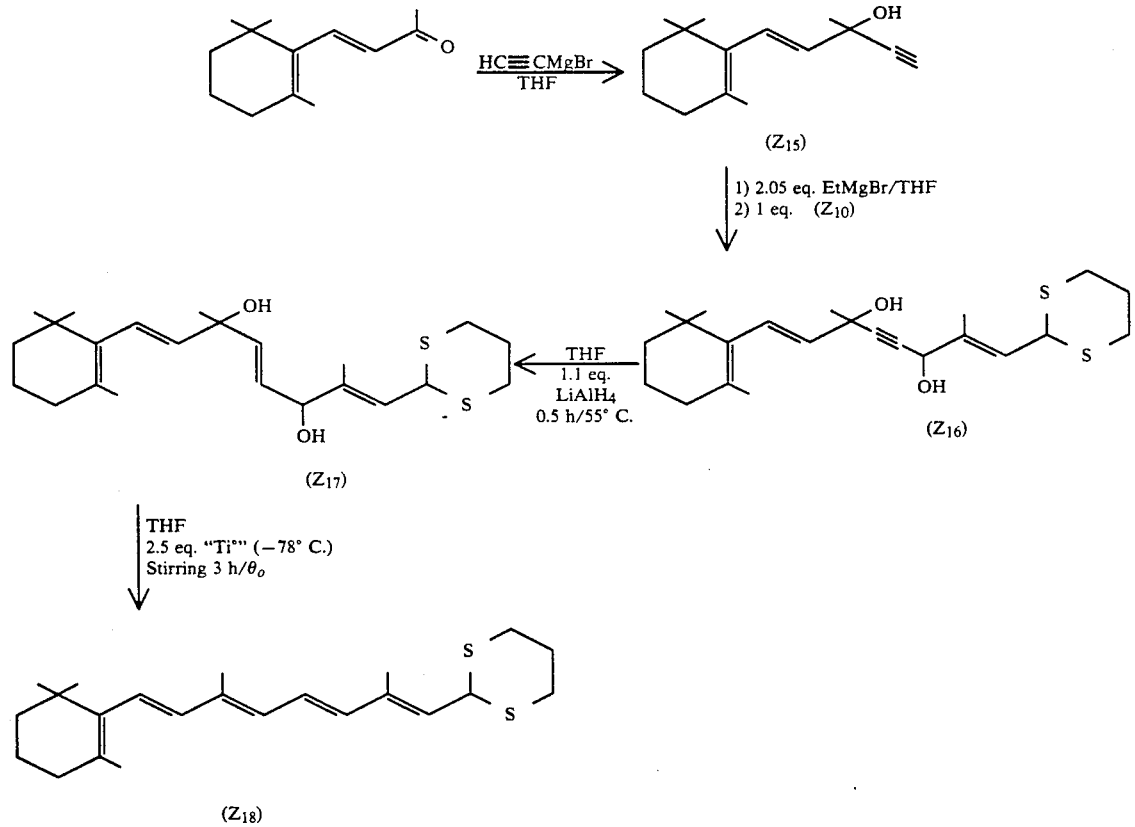

In this scheme, the intermediate compounds are designated by the references ($Z_i$), i being an integer ranging from 15 to 18; $\Theta_o$ denotes room temperature.

1st step: Preparation of ethynyl-$\beta$-ionol ($Z_{15}$) of formula:

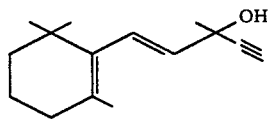

Dry magnesium (5.1 g–0.210 mol) and anhydrous tetrahydrofuran (THF) (100 ml) are placed in a 250-cm$^3$ three-necked flask equipped with a dropping funnel and a condenser. A solution of ethyl bromide (15.7 ml–0.210 mol) in anhydrous THF (30 ml) is then added slowly under argon. After reaction of the magnesium, the medium is maintained for 1 hour at room temperature.

In addition, a 500-cm$^3$ three-necked flask is equipped with a condenser connected to an oil-filled bubbling device, with a dropping funnel and with a gas diffuser for acetylene (the acetylene passing beforehand through a trap at $-78°$ C.). Acetylene is then dissolved for 1 h in anhydrous THF (200 ml) at between $-30°$ and $-20°$ C. After the cooling bath has been removed, the magnesium derivative is rapidly added dropwise, a stream of acetylene still being maintained. The temperature is maintained below 35° C.

After addition of the magnesium derivative, the medium is stirred for 30 minutes at room temperature. $\beta$-Ionone (21.2 ml–0.104 mol), dissolved in anhydrous THF (20 ml), is then added dropwise over 30 minutes. With the stream of acetylene still maintained, reaction is complete after one hour, and the yellow-green solution obtained is poured slowly into saturated NH$_4$Cl solution (250 ml). The medium is extracted with ether (3×50 ml), washed with water (50 ml) and then with saturated NaCl solution (100 ml), dried over Na₂SO₄ and finally concentrated. The residue is distilled (125° C./395 pascals) in order to obtain a colourless oil. 18.16 g of product are obtained. The compound is stored in a freezer protected from light.

The yield is 80%.

The characteristics of the product obtained are as follows:
a) TLC (hexane/ethyl acetate, 70:30) Rf≈0.64
b) M.p.=21° C.
c) M=218.34
d) The structure was confirmed by (¹H and ¹³C) NMR (200MHz) (CDCl₃) and by IR.

2nd step: Preparation of the compound ($Z_{16}$) of formula:

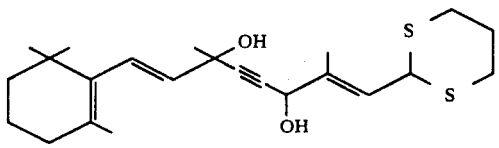

Initially, a Grignard reagent is prepared from 2.05 equivalents of magnesium (1.13 g–0.047 mol) in anhydrous tetrahydrofuran (THF) (20 ml) and under argon. 2.1 equivalents of bromoethane, dissolved in anhydrous THF (20 ml), are added dropwise. As soon as all the magnesium has dissolved, 1 equivalent of the compound ($Z_{15}$) (5 g–0.0229 mol), dissolved in THF (40 ml), is added slowly. An evolution of ethane is observed. After 1.5 h of reaction at room temperature, 1 equivalent of aldehyde ($Z_{10}$) (4.31 g–0.0229 mol), dissolved in THF (40 ml), is added rapidly to the medium. After 1 h, when it is established by thin-layer chromatography that the content of compound ($Z_{16}$) is no longer changing, the medium is hydrolysed by the slow addition of saturated NH₄Cl solution (40 ml) and then water (40 ml).

The aqueous phase is extracted with ether (3×80 ml). The combined organic phases are washed with saturated NaCl solution (100 ml), dried over Na₂SO₄ and then concentrated. The residue is purified by flash chromatography (eluent=hexane/ethyl acetate, 85:15). 6.80 g of a very "frothy" yellow oil are obtained The latter may be stored for several months in a freezer, but degrades very quickly at room temperature.

The characteristics of the product obtained are as follows:
a) TLC (hexane/ethyl acetate, 70:30) Rf≈0.24
b) M=406.66
c) The structure was confirmed by (¹H) NMR (200MHz) (CDCl₃) and by IR.

3rd step: Preparation of the compound ($Z_{17}$) of formula:

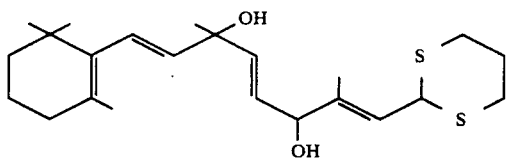

1.1 equivalents of LiAlH₄ (13.6 ml of 1.29M solution in ether) are added dropwise to 1 equivalent of the compound ($Z_{16}$) (6.5 g–0.016 mol) dissolved in anhydrous tetrahydrofuran (800 ml) under argon. When the addition is complete, the flask equipped with a condenser is immersed in a bath heated beforehand to 55° C. At this temperature, the yellow medium gradually assumes a violet colour. After 0.5 h, reaction is complete and the medium is cautiously hydrolysed by adding saturated NH₄Cl solution (150 ml), followed by water (50 ml). The aqueous phase is extracted with ether (3×100 ml). The combined organic phases are washed with saturated NaCl solution (100 ml), dried over Na₂SO₄ and then concentrated. The residue is purified by flash chromatography (eluent=hexane/ethyl acetate, 90:10). 4.6 g of a yellow oil are obtained. The latter may be stored for several months in a freezer, but degrades very quickly at room temperature.

The yield is 70%.

The characteristics of the product obtained are as follows:
a) TLC (hexane/ethyl acetate, 70:30) Rf≈0.20
b) M=408.67
c) The structure was confirmed by (¹H) NMR (200MHz) (CDCl₃) and by IR.

4th step: Production of the retinoid ($Z_{18}$) of formula (II):

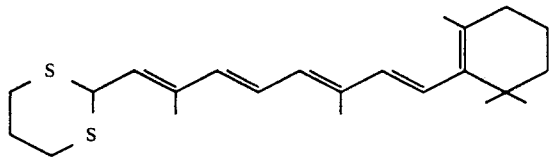

To prepare the reagent, titanium trichloride (3 g–0.019 mol) is weighed into a dry round-bottomed flask. The flask is purged with argon, and anhydrous tetrahydrofuran (70 ml) and then 0.5 equivalent of LiAlH₄ (7.5 ml of 1.29M solution in ether) are added. The mixture is stirred for 15 minutes at room temperature.

Protected from light, 2.5 equivalents of this reagent (55 ml of the suspension) are added dropwise and at −78° C. to 1 equivalent of compound ($Z_2$) (2.2 g–5.38 mmol) dissolved in anhydrous THF (50 ml). After the cold bath has been removed, the medium is stirred for 3 h at room temperature and then hydrolysed slowly at −30° C. by adding water (250 ml). The aqueous phase is extracted with ether (4×100 ml). The combined organic phases are washed with saturated NaCl solution (100 ml), filtered through a thin layer of Celite, dried over Na₂SO₄ and then concentrated under vacuum at room temperature. The yellow precipitate (1.2 g) obtained is recrystallised in methanol with the addition of a few drops of ether.

The yield is 60%.

The characteristics of the retinoid obtained are as follows:
a) TLC (hexane/ethyl acetate, 70:30) Rf≈0.75
b) M.p.=108°–110° C.
c) M=374.66
d) The structure was confirmed by (¹H and ¹³C) NMR (200MHz) (CDCl₃) and by IR.
e) Elemental analysis gives the following results:

| % | Calculated | Found |
|---|---|---|
| C | 73.74 | 73.73 |
| H | 9.15 | 9.25 |

EXAMPLE 2

Preparation of the Retinoid of Formula (III)

A) Preparation of the Starting Synthon of Formula (VIb)

The preparation is performed according to the scheme below:

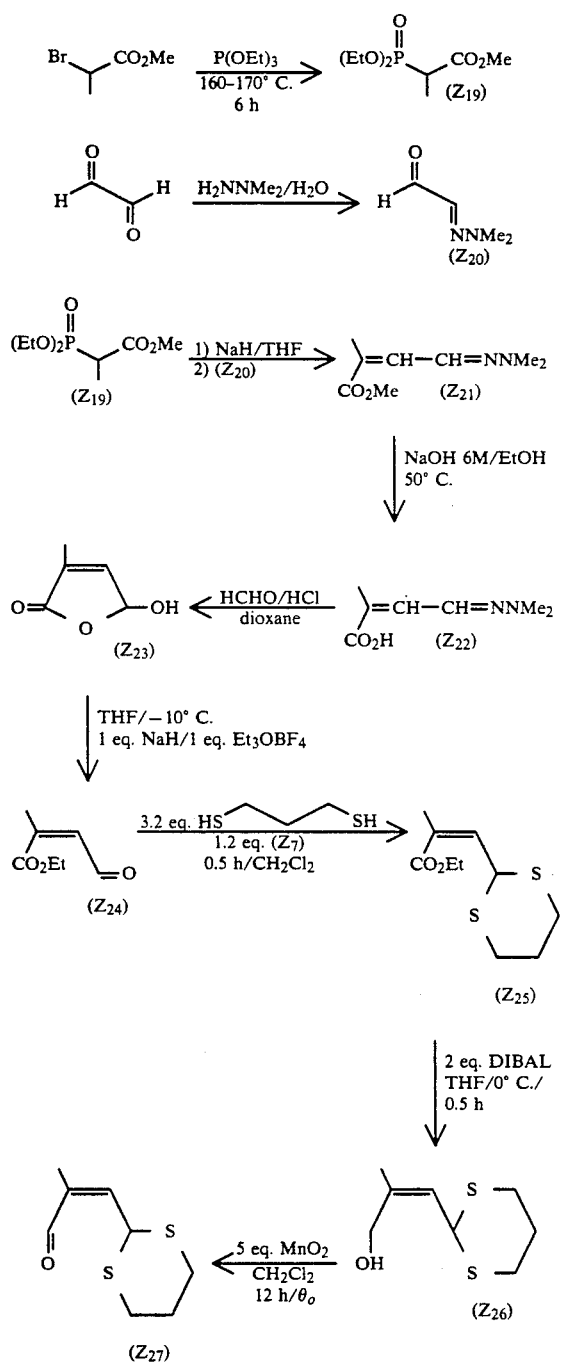

In this scheme, the intermediate compounds are designated by the references ($Z_i$), i being an integer ranging from 19 to 27; $\Theta_0$ denotes room temperature.

1st step: Preparation of methyl diethylphosphonopropionate ($Z_{19}$) of formula:

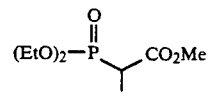

One equivalent of methyl 2-bromopropionate 10 (22.5 ml–0.2 mol) is mixed with 1.5 equivalents of triethyl phosphite (51.5 ml–0.3 mol). The mixture is heated gradually to 160°–170° C. This temperature is maintained for 6 hours. During the reaction, the ethyl bromide formed distils off (boiling point=40° C.), as does methyl acrylate (boiling point=80° C.). The excess reagent is then distilled under vacuum (60°–65° C. at 66 pascals). The phosphonopropionate is distilled (75°–80° C. at 66 pascals) in order to obtain 44.84 g of a colourless liquid.

The characteristics of the product obtained are as follows:

a) TLC (hexane/ethyl acetate, 70:30) Rf≃0.17
b) M=224.2
c) The structure was confirmed by ($^1$H and $^{13}$C) NMR (200MHz) (CDCl$_3$) and by IR.

2nd step: Preparation of glyoxal mono (N,N-dimethyl-hydrazone) ($Z_{20}$) of formula:

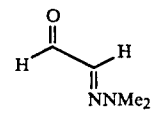

with Me=methyl 1 equivalent of N,N-dimethylhydrazine (34.2 ml–0.45 mol) is added dropwise and with stirring to 1.1 equivalents of glyoxal (0.5 mol–29 ml of reagent in 30% aqueous solution) in water (300 ml). After 0.5 h at room temperature, the medium is extracted with CH$_2$Cl$_2$ (3×150 ml). The combined organic phases are dried over Na$_2$SO$_4$ and then concentrated. The light-yellow liquid (45 g) obtained is used without further treatment.

The characteristics of the product obtained are as follows:

a) TLC (hexane/ethyl acetate, 70:30) Rf≃0.23
b) M=100.12
c) The structure was confirmed by ($^1$H) NMR (200MHz) (CDCl$_3$) and in IR.

3rd step: Preparation of methyl 4-(N,N-dimethylhydrazono)-2-methyl-2-butenoate ($Z_{21}$) of formula:

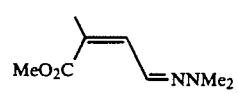

with Me=methyl

Sodium hydride (1.07 g–0.0446 mol) is suspended in anhydrous tetrahydrofuran (THF) (40 ml). The medium is cooled to 0° C. and 1 equivalent of the stirring (10 g–0.0446 mol). After 5 minutes, 1 equivalent of the hydrazone ($Z_{20}$) (4.46 g–0.0446 mol) is added slowly to the medium. A yellow-brown gum deposits rapidly at the bottom of the reaction flask. The reaction is monitored by thin-layer chromatography until the starting materials have completely disappeared (15 to 30 minutes). The medium is then hydrolysed by adding water (10 ml), and thereafter extracted with ether (3×50 ml). The combined organic phases are washed with saturated NaCl solution (50 ml), dried over $Na_2SO_4$ and then concentrated. The residue is recrystallised in an acetone/pentane mixture; if it is too impure, it must be subjected to flash chromatography (eluent=hexane/ethyl acetate, 80:20; silica treated with 3% of triethylamine). 7.21 g of product are obtained after recrystallisation.

The yield is 95%.

The characteristics of the product obtained are as follows:
a) TLC (hexane/ethyl acetate, 70:30) $Rf \approx 0.56$
b) M.p. = 49°-50° C.
c) M = 170.2
d) The structure was confirmed by ($^1H$ and $^{13}C$) NMR (200 MHz) ($CDCl_3$) and by IR.
e) Elemental analysis gives the following results:

| % | Calculated | Found |
|---|---|---|
| C | 56.46 | 56.28 |
| H | 8.29 | 8.40 |
| N | 16.46 | 16.40 |

4th step: Preparation of 4-(N,N-dimethylhydrazono)-2-methyl-2-butenoic acid ($Z_{22}$) of formula:

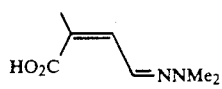

with Me=methyl

The ester ($Z_{22}$) (10 g–0.059 mol) is dissolved in a 1:1 mixture of ethanol and 6M caustic soda (800 ml). The reaction mixture is then stirred at 50° C. until the starting material has disappeared (30 min). It is then diluted by adding water (100 ml), and the bulk of the alcohol is evaporated off under vacuum. The residue is extracted a first time with ether (2×100 ml) in order to remove all organic degradation products. After a further addition of ether (200 ml) to the aqueous phase, the latter is acidified by the slow addition of concentrated sulphuric acid while monitoring the pH. As soon as a pH of 3.4 is reached, the reaction mixture is extracted with ether (3×100 ml), dried over $Na_2SO_4$ and then concentrated. The residue is recrystallised in an acetone/pentane mixture. 8.75 g of product are obtained in the form of long, pale yellow needles.

The yield is 95%.

The characteristics of the product obtained are as follows:
a) TLC (hexane/ethyl acetate, 70:30) $Rf \approx 0.07$
b) M.p. = 145°-147° C.
c) M = 156.19
d) The structure was confirmed by ($^1H$ and $^{13}C$) NMR (200 MHz) ($CDCl_3$) and by IR.
e) Elemental analysis gives the following results:

| % | Calculated | Found |
|---|---|---|
| C | 53.83 | 54.00 |
| H | 7.74 | 7.73 |
| N | 17.94 | 18.19 |

5th step: Preparation of 5-hydroxy-3-methyl-2(5H)-furanone ($Z_{23}$) of formula:

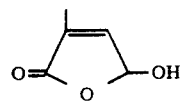

18 ml of 35% formaldehyde in water and 13 ml of concentrated hydrochloric acid are added to the hydrazone ($Z_{22}$) (6.5 g–0.0416 mol) dissolved in dioxane (130 ml). The medium is stirred at room temperature until the starting material has disappeared (5 to 6 h). It is then poured onto crushed ice and organic phase is dried over $Na_2SO_4$ and then concentrated.

The butenolide obtained is purified by flash chromatography (eluent=hexane/ethyl acetate/ether, 40:30:30). 3.75 g of beige crystals are obtained.

The yield is 79%.

The characteristics of the product obtained are as follows:
a) TLC (hexane/ethyl acetate, 50:50) $Rf \approx 0.29$
b) M.p. = 70°-72° C.
c) M = 114.1
d) The structure was confirmed by ($^1H$ and $^{13}C$) NMR (200 MHz) ($CDCl_3$) and by IR.
e) Elemental analysis gives the following results:

| % | Calculated | Found |
|---|---|---|
| C | 52.63 | 52.82 |
| H | 5.30 | 5.33 |

6th step: Preparation of triethyloxonium tetrafluoroborate ($Et_3OBF_4$)

0.75 equivalent of epichlorohydrin (14.2 ml–0.182 mol) is added dropwise and with vigorous stirring to freshly distilled boron trifluoride etherate (30 ml–0.243 mol) dissolved in anhydrous ether (60 ml) under argon, in such a way that spontaneous refluxing takes place. This reflux is maintained for 1 h and the medium is then left standing overnight. A translucent gel deposits at the bottom of the reaction flask. It is filtered off under argon, washed copiously with anhydrous ether and then dried using a vane pump. A white precipitate of 26 g of triethyloxonium tetrafluoroborate is obtained It may be stored for several days in a refrigerator under argon.

The yield is 78%.

The molecular mass is M = 183.94

7th step: Preparation of ethyl β-formylmethacrylate in cis form ($Z_{24}$), of formula:

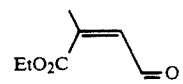

with Et=ethyl

The butenolide ($Z_{23}$) (3 g–0.026 mol) is solubilised in distilled methylene chloride (60 ml). After the medium is cooled to −10° C., 1 equivalent of sodium hydride (0.624 g–0.026 mol) is added, followed immediately by 1 equivalent of triethyloxonium tetrafluoroborate (4.97 g–0.026 mol). The medium is stirred for 1.5 h at −10° C. to approximately 5° C. before being hydrolysed by adding one equivalent of triethylamine (3.6 ml–0.026 mol) and 30 ml of anhydrous ether. The pale yellow precipitate formed (complex of triethylamine and boron trifluoride) is filtered off and washed copiously with anhydrous ether. The residue is evaporated and then treated by chromatography on a silica column (eluent=hexane/ethyl acetate, 80:20; silica treated with 3% of triethylamine). 2.22 g of a yellow oil are obtained.

The yield is 60%.

The characteristics of the product are as follows:
a) TLC (hexane/ethyl acetate, 70:30)
b) M=142.16
c) The structure was confirmed by ($^1$H and $^{13}$C) NMR (200 MHz) (CDCl$_3$) and by IR.
d) Elemental analysis gives the following results:

| % | Calculated | Found |
| --- | --- | --- |
| C | 59.14 | 58.88 |
| H | 7.09 | 7.21 |

8th step: Preparation of ethyl β-(1,3-dithianyl)methacrylate in cis form (Z$_{25}$), of formula:

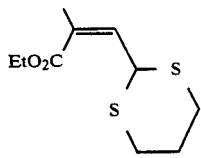

with Et=ethyl 3.2 equivalents of 1,3-propanedithiol (4.85 ml–0.048 mol) and 1.2 equivalents of Zn(OTf)$_2$ (compound (Z$_7$) obtained as described in Example 1) (6.54 g–0.018 mol) are dissolved in distilled CH$_2$Cl$_2$ (80 ml) under argon. After the medium is stirred for 15 minutes at room temperature, 1 equivalent of the aldehyde (Z$_{24}$) (2.2 g–0.015 mol), dissolved in CH$_2$Cl$_2$ (20 ml), is rapidly added dropwise. Reaction is complete after 0.5 h, and the medium is diluted by adding water (90 ml) and then saturated NH$_4$Cl solution until a pH of between 4 and 5 is reached (approximately 200 ml). The aqueous phase is extracted with a hexane/ether (1:1) mixture (4×100 ml). The combined organic phases are washed with saturated NH$_4$Cl solution (100 ml) in order to "break" the emulsion which has formed, then with 0.5M caustic soda (3×100 ml), with saturated NaHCO$_3$ solution (100 ml), with water (2×100 ml) and finally with saturated NaCl solution (100 ml). After drying over Na$_2$SO$_4$ and evaporation of the solvent, 3.6 g of a colourless oil are isolated.

The characteristics of the product obtained are as follows:
a) TLC (hexane/ethyl acetate, 90:10) Rf≈0.36
b) M=232.37
c) The structure was confirmed by ($^1$H and $^{13}$C) NMR (200 MHz) (CDCl$_3$) and by IR.
d) Elemental analysis gives the following results:

| % | Calculated | Found |
| --- | --- | --- |
| C | 51.69 | 51.83 |
| H | 6.94 | 6.85 |

9th step: Preparation of the compound (Z)-3-(1,3-dithian-2-yl)-2-methylpropenol (Z$_{26}$) of formula:

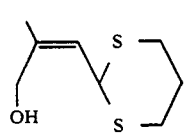

| % | Calculated | Found |
| --- | --- | --- |
| C | 51.69 | 51.83 |
| H | 6.94 | 6.85 |

The ester (Z$_{25}$) (3.5 g–0.015 mol) is dissolved in anhydrous tetrahydrofuran (THF) (70 ml) under argon. After the medium is cooled to 0° C., 2.2 equivalents of diisobutylaluminium hydride (DIBAL) (33 ml of 1M solution in toluene) are rapidly added dropwise. After 0.5 h, reaction is complete and the medium is hydrolysed by the slow addition of methanol (1.55 ml). The mixture is poured into a mixture of ethyl acetate (600 ml) and saturated sodium tartrate solution (74 ml). Vigorous stirring of this medium for 1 h enables the gel which has formed to be "broken". The aqueous phase is then extracted with ethyl acetate (3×100 ml). The combined organic phases are washed with saturated NaCl solution (100 ml), dried over Na$_2$SO$_4$ and then concentrated. The residue is treated by chromatography on a silica column (eluent=hexane/ethyl acetate, 80:20; silica treated with 3% of triethylamine) to give 2.30 g of a colourless oil.

The yield is 81%.

The characteristics of the product obtained are as follows:
a) TLC (hexane/ethyl acetate, 70:30) Rf≈0.23
b) The structure was confirmed by ($^1$H and :$^{13}$C) NMR (200 MHz) (CDCl$_3$) and by IR.
c) Elemental analysis gives the following results:

| % | Calculated | Found |
| --- | --- | --- |
| C | 50.49 | 50.69 |
| H | 7.41 | 7.69 |

10th step: Preparation of the synthon consisting of (Z)-3-(1,3-dithian-2-yl)-2-methylpropenal (Z$_{27}$) of formula:

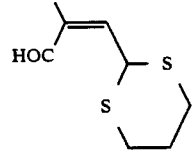

The alcohol (Z$_{26}$) (2.3 g–0.012 mol) is dissolved in distilled CH$_2$Cl$_2$ (150 ml) under argon. Approximately 5 equivalents of manganese dioxide (5.25 g) are added to the medium with vigorous stirring. After 4 h at room temperature, the suspension is filtered through a thin layer of silica. The silica is washed copiously with ethyl acetate. The filtrate concentrated under vacuum. 2.15 g of beige crystals are obtained.

The yield is 95%.

The characteristics of the product are as follows:
a) TLC (hexane/ethyl acetate, 70:30) Rf≈0.52 b) M.p. = 102° C.
c) M = 188.32
d) The structure was confirmed by ($^1$H and $^{13}$C) NMR (200MHz) (CDCl$_3$) and by IR.
e) Elemental analysis gives the following results:

| % | Calculated | Found |
|---|---|---|
| C | 51.02 | 51.20 |
| H | 6.42 | 6.47 |

B) Preparation of the Retinoid of Formula (III)

The preparation is performed according to the following reaction scheme:

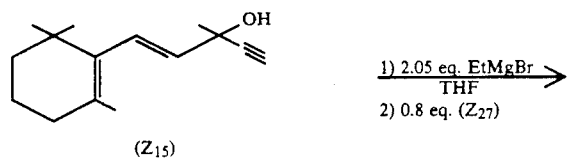

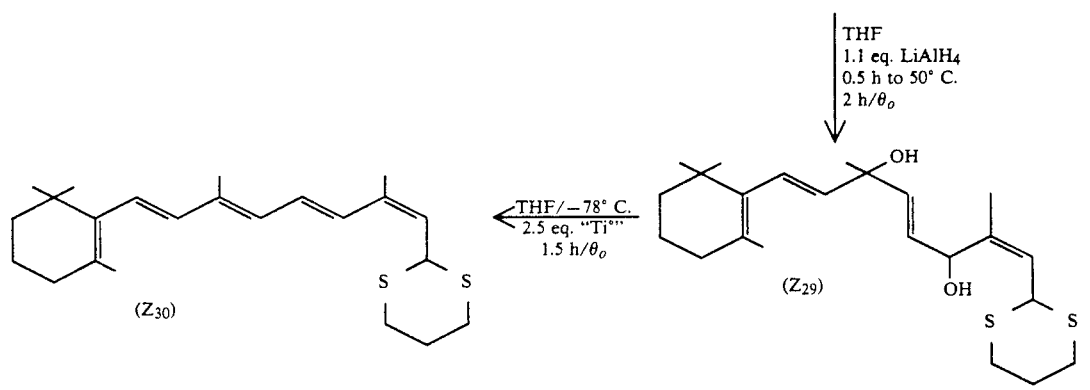

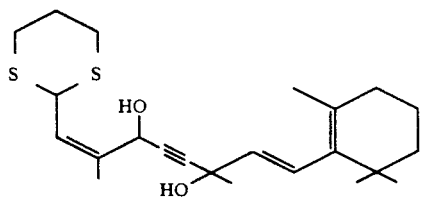

The compound ($Z_{15}$) is prepared as described in Example 1.

In this scheme, the intermediate compounds are designated by the references ($Z_i$), i being an integer ranging from 28 to 30. $\Theta_0$ denotes room temperature.

1st step: Preparation of the compound ($Z_{28}$) of formula:

Initially, a Grignard reagent is prepared from 2.05 equivalents of magnesium (79.2 mg-3.26 mmol) in anhydrous tetrahydrofuran (THF) (10 ml) and under argon. 2.1 equivalents of bromoethane (0.25 ml-3.34 mmol), dissolved in anhydrous THF (10 ml), are added dropwise. As soon as the magnesium has dissolved, 1 equivalent of the compound ($Z_{15}$) (348 mg-159 mmol), dissolved in THF (10 ml), is added slowly. An evolution of ethane is observed. After 2 h of reaction at room temperature, 0.8 equivalent of the compound ($Z_{27}$) (0.24 g-1.275 mmol), dissolved in THF (10 ml), is added rapidly to the medium. After 1.5 h, when it is established by thin-layer chromatography that the content of compound ($Z_{28}$) is no longer changing, the medium is hydrolysed by the slow addition of saturated NH$_4$Cl solution (20 ml; pH 7) and then water (3×50 ml). The combined organic phases are washed with saturated NaCl solution (80 ml), dried over Na$_2$SO$_4$ and then concentrated. The residue is purified by flash chromatography (eluent=hexane/ethyl acetate, 80:20). 430 mg of a very "frothy" yellow oil are obtained, which oil may be stored for several months in a freezer but degrades very rapidly at room temperature.

The yield is 83% relative to the compound ($Z_{27}$).

The characteristics of the product obtained are as follows:

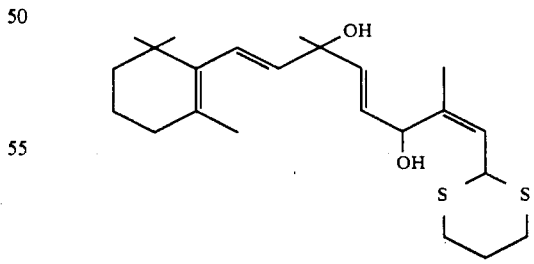

a) TLC (hexane/ethyl acetate, 70:30) Rf≃0.24
c) M=406.66
d) The structure was confirmed by ($^1$H) NMR (200 MHz) (CDCl$_3$) and by studying the infrared spectrum (CCl$_4$).

2nd step: Preparation of the compound ($Z_{29}$) of formula:

1.4 equivalents of LiAlH$_4$ (1.1 ml of 0.89M solution in ether) are added dropwise to 1 equivalent of the compound ($Z_{28}$) (350 mg-0.86 mmol) dissolved in anhydrous tetrahydrofuran (THF) (35 ml) under argon. When the addition is complete, the reaction flask equipped with a condenser is immersed in a bath heated beforehand to 50° C. At this temperature, the yellow medium gradually darkens. After 1.5 h, since the medium is becoming excessively degraded, stirring is continued at room temperature for 2 h. The medium is then cautiously hydrolysed by adding saturated NH4Cl solution (20 ml; pH 7) and then water (10 ml). The aqueous phase is extracted with ether (3×20 ml). The combined organic phases are washed with saturated NaCl solution (50 ml), dried over Na2SO4, and then concentrated. The residue is purified by flash chromatography (eluent-=hexane/ethyl acetate, 90:10). 105 mg of a yellow oil are obtained; this oil may be stored with difficulty in a freezer and degrades very quickly at room temperature.

The yield is 55%.

The characteristics of the product obtained are as follows:
a) TLC (hexane/ethyl acetate, 70:30) Rf≃0.23
b) M=408.67
c) The structure was confirmed by ($^1$H) NMR (200 MHz) (CDCl3)

3rd step: Preparation of the retinoid ($Z_{30}$) of formula (III):

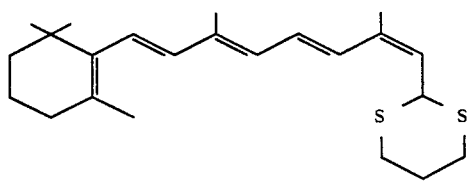

To prepare the reagent containing low-valency titanium (Ti°), titanium trichloride (1.5 g-9.72 mmol) is weighed into a dry round-bottomed flask equipped with a condenser; the flask is purged with argon, and anhydrous tetrahydrofuran (THF) (48 ml) is added, followed by 0.5 equivalent of LiAlH4 (2.2 ml of 2.2M solution in ether). The medium is stirred for 10 minutes at room temperature, 0.42 equivalent of triethylamine (0.57 ml-4.08 mmol) is then added and the mixture is heated to reflux for 1.5 h.

Protected from light, 2.1 equivalents of the reagent obtained (3.7 ml of the suspension) are added dropwise and at −78° C. to 1 equivalent of compound ($Z_{29}$) (0.14 mg-0.343 mmol) dissolved in anhydrous THF (20 ml). The medium is then immersed in a bath at 50° C. and stirred for 0.5 h at this temperature, and thereafter hydrolysed slowly at −30° C. by adding water (10 ml). The aqueous phase is extracted with ether (4×15 ml). The combined organic phases are filtered through a thin layer of Celite, dried over Na2SO4 and then concentrated under vacuum. The residue obtained is purified by flash chromatography (eluent: hexane/ether, 95:5). 64 mg of yellow crystals are obtained.

The yield is 50%.

The characteristics of the product obtained are as follows:
a) TLC (hexane/ethyl acetate, 70:30) Rf≃0.80
b) M=374.66
c) The structure was confirmed by ($^1$H) NMR (200MHz) (CDCl3).

EXAMPLE 3

Preparation of the Retinoid of Formula (IV)

A) Preparation of the Synthon of Formula (VIc)

The preparation is performed according to the following scheme:

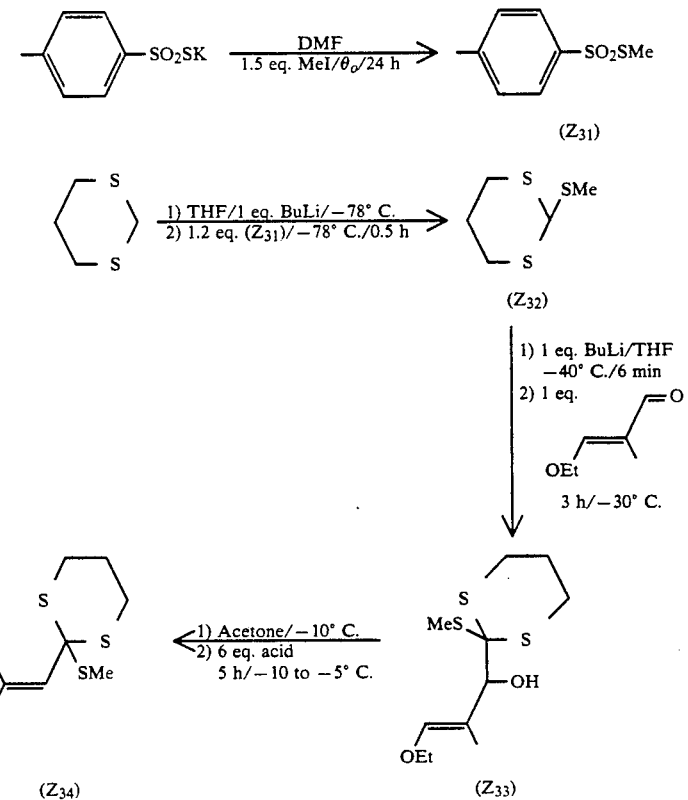

In this scheme, the intermediate compounds are designated by the references ($Z_i$), i being an integer ranging from 31 to 34; $\Theta_0$ denotes room temperature.

1st step: Preparation of S-methyl 4-methylbenzenethiosulphonate ($Z_{31}$) of formula:

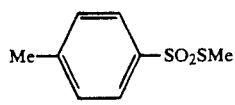

with Me=methyl 1.3 equivalents of iodomethane (12.8 ml–0.201 mol) are rapidly added dropwise to 1 equivalent of potassium toluenethiosulphonate (35 g–0.155 mol) dissolved in dimethylformamide distilled on 4-angstrom molecular sieve (500 ml). The medium is stirred for 24 h at room temperature. During reaction, it gradually turns brown. After dilution by adding water (450 ml), the medium is extracted with $CH_2Cl_2$ (5×150 ml). The combined organic phases are washed with saturated $NaHCO_3$ solution (2×150 ml) and with saturated $Na_2SO_3$ solution (200 ml), enabling the medium to be decolorised, and then washed copiously with water (5×200 ml). After a final wash with saturated NaCl solution (250 ml), followed by drying over $Na_2SO_4$ and concentration, a yellow precipitate is obtained. It is recrystallised in ether with the addition of a little pentane. 27.91 g of large white crystals are obtained.

The yield is 89%.

The characteristics of the product obtained are as follows:
a) TLC (hexane/ethyl acetate, 70:30) Rf≃0.5
b) M.p.=58°–59° C.
c) M=202.3
d) The structure was confirmed by ($^1H$ and $^{13}C$) NMR (200MHz) ($CDCl_3$) and by IR.

2nd step: Preparation of 2-methylthio-1,3-dithiane ($Z_{32}$) of formula:

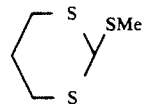

with Me=methyl

A solution of 1,3-dithiane (6 g–0.05 mol) in anhydrous tetrahydrofuran (THF) (200 ml) is cooled to −78° C.; 1 equivalent of n-butyllithium (33.3 ml of 1.5M solution) is rapidly added dropwise. The medium is stirred for 2 h at this temperature; it is then added via a narrow tube to 1.2 equivalents of compound ($Z_{31}$) (12.14 g–0.06 mol) dissolved in anhydrous THF (80 ml) at −78° C. During the addition (which takes place in the course of approximately 35 minutes), a white precipitate gradually forms. Stirring is maintained at −78° C. for 0.5 h, and the medium is then hydrolysed by adding 0.05N HCl (600 ml). The THF is evaporated off and the residue is then extracted with a $CH_2Cl_2$/pentane (1:1) mixture (4×200 ml). The combined organic phases are washed with saturated $NaHCO_3$ solution (3×100 ml) and with saturated NaCl solution (250 ml), then dried over $Na_2SO_4$ and concentrated. The residue is rapidly subjected to chromatography on a silica column (eluent=hexane/ether, 95:5) in order to remove the excess methyl toluenethiosulphonate ($Z_{31}$) 7.90 g of a colourless oil, which precipitates in the freezer, are obtained.

The yield is 95%.

The characteristics of the product obtained are as follows:
a) TLC (hexane/ether, 90:10) Rf≃0.54
b) M=166.33
c) The structure was confirmed by ($^1H$ and $^{13}C$) NMR (200MHz) ($CDCl_3$)

3rd step: Preparation of ethyl 3-(2-methylthio-1,3-dithian-2-yl)-3-hydroxy-2-methyl-1-propenyl ether ($Z_{33}$) of formula:

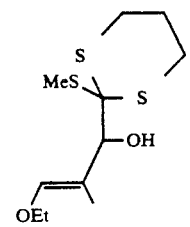

Me=methyl
Et=ethyl 1 equivalent of n-butyllithium (30 ml of 1.5M solution) is rapidly added dropwise to the ortho thioester ($Z_{32}$) (7.5 g–0.045 mol) dissolved in distilled tetrahydrofuran (THF) (150 ml) at −40° C. After 6 minutes of reaction at this temperature, 1 equivalent of ethoxymethacrolein (5.35 ml–0.045 mol) is added. Stirring is maintained for 3 h at −30° C., and the medium is then hydrolysed by adding saturated $NH_4Cl$ solution (approximately 200 ml-pH 5). As soon as the extracted with ether (3×200 ml). The combined organic phases are washed with saturated $NaHCO_3$ solution (2×200 ml), water (200 ml) and saturated NaCl solution (200 ml), then dried over $Na_2SO_4$ and concentrated. The yellow residue is purified by flash chromatography (eluent=hexane/ether, 90:10). 10.25 g of a light-yellow oil are obtained, which oil is stored in a freezer, in which it precipitates.

The yield is 81%.

The characteristics of the product obtained are as follows:
a) TLC (hexane/ether, 90:10) Rf≃0.12
b) M.p.=39°–40° C.
c) M=280.48
d) The structure was confirmed by ($^1H$ and $^{13}C$) NMR (200MHz) ($CDCl_3$) and by IR.
e) Elemental analysis gives the following results:

| % | Calculated | Found |
|---|---|---|
| C | 47.11 | 47.37 |
| H | 7.19 | 7.22 |

4th step: Preparation of (E)-3-(2-methylthio-1,3-dithian-2-yl)-2-methylpropenal ($Z_{34}$) of formula:

B) Preparation of the Retinoid of Formula (IV)

The preparation is performed according to the scheme below.

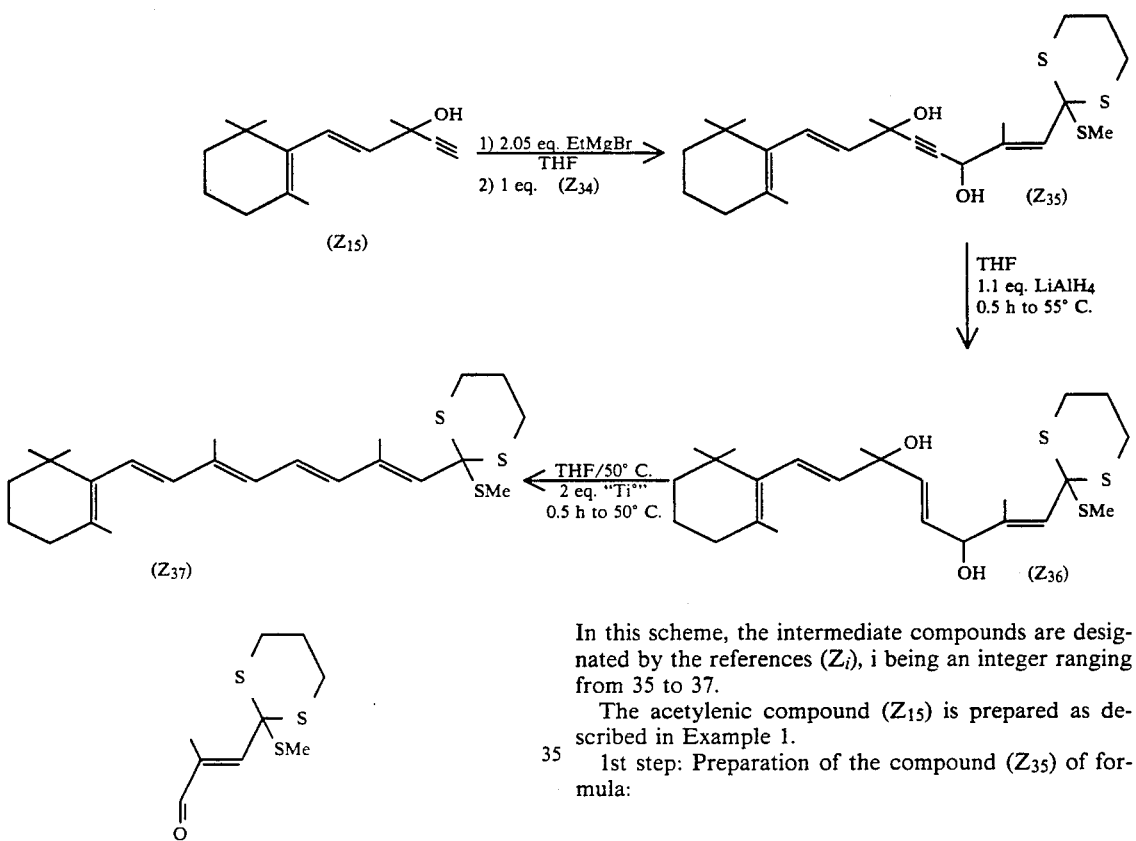

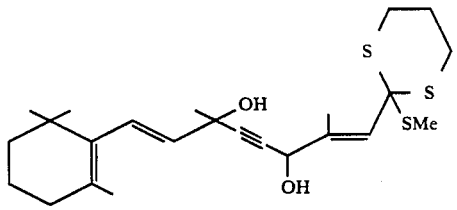

with Me = methyl

The enol ether ($Z_{33}$) (9 g-0.032 mol) is dissolved in acetone (300 ml) at $-10°$ C.; 6 equivalents of acid (54 ml of 10% sulphuric acid in water) are added slowly to the medium. The latter is stirred for 5 h at between $-10$ and $-5°$ C. before being hydrolysed by adding saturated NaHCO$_3$ solution (approximately 200 ml; pH 5) and water (200 ml). The acetone is evaporated off and the medium is then extracted with ether (5 × 100 ml).

The combined organic phases are washed with saturated NaHCO$_3$ solution (70 ml; pH 7) and saturated NaCl solution (250 ml). After drying over Na$_2$SO$_4$ and concentration, the residue is purified by flash chromatography (eluent = hexane/ether, 90:10). 5.62 g of a yellow oil are obtained.

The yield is 75%.

The characteristics of the product obtained are as follows:
a) TLC (hexane/ether, 90:10) Rf≈0.28
b) M = 234.41
c) The structure was confirmed by ($^1$H and $^{13}$C) NMR (200MHz) (CDCl$_3$) and by IR.
d) Elemental analysis gives the following results:

| % | Calculated | Found |
|---|---|---|
| C | 46.12 | 46.22 |
| H | 6.02 | 5.95 |

In this scheme, the intermediate compounds are designated by the references ($Z_i$), i being an integer ranging from 35 to 37.

The acetylenic compound ($Z_{15}$) is prepared as described in Example 1.

1st step: Preparation of the compound ($Z_{35}$) of formula:

with Me = methyl

Initially, a Grignard reagent is prepared from 2.05 equivalents of magnesium (1.13 g-0.047 mol) in anhydrous tetrahydrofuran (THF) (20 ml) and under argon. 2.1 equivalents of bromoethane (3.6 ml-0.048 mol), dissolved in anhydrous THF (20 ml), are added dropwise. As soon as all the magnesium has dissolved, 1 equivalent of the compound ($Z_{15}$) (5 g-0.0229 mol), dissolved in THF (50 ml), is added slowly. An evolution of ethane is observed. After 1.5 h of reaction at room temperature, 1 equivalent of aldehyde ($Z_{34}$) (5.37 g-0.0229 mol), dissolved in THF (50 ml), is added rapidly to the medium. After 1 h, when it is established by thin-layer chromatography that the content of compound ($Z_{35}$) is no longer changing, the medium is hydrolysed by the slow addition of saturated NH$_4$Cl solution (50 ml), followed by water (50 ml). The aqueous phase is extracted with ether (3 × 80 ml). The combined organic phases are washed with saturated NaCl solution (100 ml), dried over Na$_2$SO$_4$ and then concentrated. The residue is purified by flash chromatography (eluent=hexane/ethyl acetate, 85:15). 9.33 g of a very "frothy" yellow oil are obtained.

The yield is 90%.

The characteristics of the product obtained are as follows:
a) TLC (hexane/ethyl acetate, 70:30) Rf≈0.29
b) M=452.75
c) The structure was confirmed by ($^1$H) NMR (200MHz) (CDCl$_3$) and by studying the IR spectrum (CCl$_4$).

2nd step: Preparation of the diol (Z$_{36}$) of formula:

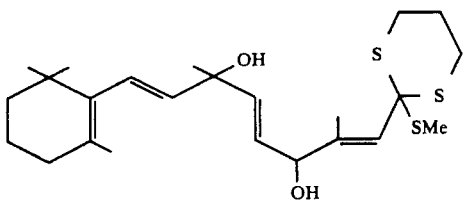

with Me=methyl 1.1 equivalents of LiAlH$_4$ (2.7 ml of 1M solution in ether) are added dropwise to 1 equivalent of the compound (Z$_{36}$) (1.1 g–2.43 mmol) dissolved in anhydrous tetrahydrofuran (THF) (140 ml) under argon. When the addition is complete, the flask equipped with a condenser is immersed in a bath heated beforehand to 55° C. At this temperature, the yellow medium gradually assumes a violet colour. After 0.5 h, reaction is complete and the medium is cautiously hydrolysed by adding saturated NH$_4$Cl solution (60 ml), followed by water (20 ml). The aqueous phase is extracted with ether (3×70 ml). The combined organic phases are washed with saturated NaCl solution (100 ml), dried over Na$_2$SO$_4$ and then concentrated. The residue is purified by flash chromatography (eluent=hexane/ethyl acetate, 90:10). 0.9 g of a yellow oil is obtained.

The yield is 81%.

The characteristics of the product obtained are as follows:
a) TLC (hexane/ethyl acetate, 70:30) Rf≈0.21
b) M=454.77
c) The structure was confirmed by ($^1$H) NMR (200MHz) (CDCl$_3$)

3rd step: Preparation of the retinoid of formula (IV):

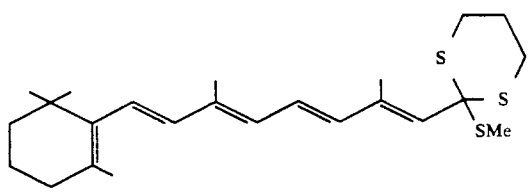

with =methyl

To prepare the reagent containing low-valency titanium (Ti°), titanium trichloride (0.5 g–3.24 mmol) is weighed into a dry round-bottomed flask equipped with a condenser. The assembly is purged with argon, and anhydrous tetrahydrofuran (THF) (80 ml) is added. 0.5 equivalent of LiAlH$_4$ (1.47 ml of 1.1M solution in ether) is then added. The medium is stirred for 10 minutes at room temperature, 0.2 equivalent of triethylamine (0.09 ml–0.648 mmol) is then added and the mixture is heated to reflux for 1.5 h.

Protected from light, 2 equivalents of the reagent containing titanium (66.4 ml of the suspension) are added dropwise and at 50° C. to 1 equivalent of compound (Z) (0.6 g–1.32 mmol) dissolved in anhydrous THF (30 ml). The medium is stirred for 0.5 h at this temperature, and is then hydrolysed slowly at −30° C. by adding water (90 ml). The aqueous phase is extracted with ether (4×80 ml). The combined organic phases are filtered through a thin layer of Celite, dried over Na$_2$SO$_4$ and then concentrated under vacuum at room temperature. The residue obtained is purified by flash chromatography (eluent=hexane/ether, 95:5). 0.82 g of a yellow oil is obtained.

The yield is 60%.

The characteristics of the product obtained are as follows:
a) TLC (hexane/ethyl acetate, 70:30) Rf≈0.86
b) M=420.76
c) The structure was confirmed by ($^1$H) NMR (200MHz) (CDCl$_3$) and by IR (CCl$_4$).

EXAMPLE 4

Hydrolysis of the Retinoid (Z$_{18}$) of Formula (IV)

1st step: Production of t-butyl N-(mesitylenesulphonyloxy)carbamate (Z$_{40}$) of formula:

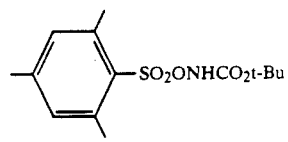

with t-Bu=tert-butyl 1 equivalent of triethylamine (3.5 ml–0.025 mol) is added dropwise to 1 equivalent of mesitylenesulphonyl chloride (5.45 g–0.025 mol) and 1 equivalent of t-butyl N-hydroxycarbamate (3.32 g–0.025 mol) dissolved in anhydrous ether (100 ml) at 0° C. During the reaction, a precipitate of triethylamine hydrochloride gradually forms. After 0.5 h of stirring at 0° C., this precipitate is filtered off and washed copiously with ether. The medium is concentrated under vacuum. 5.01 g of pale yellow residue are obtained, which product is recrystallised twice in a minimum amount of hot benzene (8 ml) and of hexane (30 ml).

The yield is 64%.

The molecular mass is:
M=315.39

2nd step: Production of O-(mesitylenesulphonyl)hydroxylamine (Z$_{41}$) of formula:

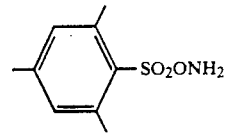

The compound (Z$_{40}$) (3 g–9.51 mmol) is added to trifluoroacetic acid (11 ml) at 5° C. Stirring is maintained for 5 minutes at this temperature and the medium is then poured into ice-cold water (80 ml). The precipitate which forms is filtered off and washed with a little cold water (30 ml). It is then dissolved in a minimum amount of ether (5 ml) and crystallised by adding hexane (15 ml). Crystallisation takes place slowly in the cold state. White crystals are obtained.

By NMR, the presence of a large amount of starting material is established; the residue (2.1 g) was hence reacted again under exactly the same conditions for 5 minutes, and the product was precipitated and recrystallised (0.74 g).

The yield is 36%.
The molecular mass is:
M=315.27

3rd step: Production of all-trans-retinal of formula:

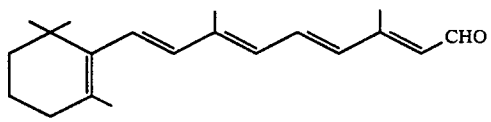

The compound ($Z_{18}$) (64 mg–$1.71 \times 10^{-4}$ mol), dissolved in $CH_2Cl_2$ (2 ml), is placed at $-95°$ C. (pentane+liquid nitrogen) and 2 equivalents of the compound ($Z_{41}$) (73.5 mg–$3.42 \times 10^{-4}$ mol), dissolved in $CH_2Cl_2$ (2 ml), are then added dropwise over 5 minutes. After 10 minutes at $-95°$ C., the medium is hydrolysed by adding ether (5 ml) and saturated NaCl solution (10 ml); the mixture is then stirred vigorously for 0.5 h. The aqueous phase is extracted with ether ($2 \times 10$ ml). The combined organic phases are washed with saturated NaCl solution ($2 \times 10$ ml), dried over $Na_2SO_4$ and then concentrated. The residue is purified by flash chromatography (eluent=hexane/ethyl acetate, 95:5). Yellow crystals are obtained (39 mg).

The yield is 80%.

The characteristics of the product obtained are as follows:
a) TLC (hexane/ethyl acetate, 70:30) Rf≃0.63
b) M=284.45

($^1$H) NMR analysis of the crude reaction product indicates the presence of a little 13-cis isomer (7%), which is removed by chromatography.

EXAMPLE 5

A gel is prepared by producing the following formulation:

| | |
|---|---|
| compound of formula (IV) | 0.050 g |
| Erythromycin base | 4.000 g |
| Butylated hydroxytoluene | 0.050 g |
| Hydroxypropylcellulose sold by the company HERCULES under the name "KLUCEL HF" | 2.000 g |
| Ethanol (95° strength) qs | 100.000 g |

This gel is applied to skin affected by dermatosis or by acne 1 to 3 times a day. After 6 to 12 weeks of treatment on the basis of 2 to 10 mg per cm$^2$ of skin treated and per application, a significant improvement is observed.

EXAMPLE 6

The following formulation, designed to be packaged in a hard gelatin capsule, is prepared:

| | |
|---|---|
| compound of formula (IV) | 0.060 g |
| Maize starch | 0.060 g |
| Lactose qs | 0.300 g |

The capsules used consist of gelatin, titanium oxide and a preservative.

1 to 3 capsules a day are administered to an adult individual in the treatment of psoriasis.

After 30 days of treatment on the basis of 1 mg per kg of body weight of the subject being treated and per day, a significant improvement is observed.

EXAMPLE 7

A gel for topical application is prepared by mixing the following ingredients:

| | |
|---|---|
| compound of formula (II) | 0.05 g |
| Ethanol | 43.00 g |
| α-Tocopherol | 0.05 g |
| Crosslinked polyacrylic acid sold by the company "GOODRICH" under the name "CARBOPOL 940" | 0.50 g |
| Triethanolamine (20% aqueous solution) | 3.80 g |
| Water | 9.30 g |
| Propylene glycol qs | 100.00 g |

This gel is applied twice a day to skin affected by acne. After 6 to 12 weeks of treatment on the basis of 2 to 10 mg per cm$^2$ of skin treated and per application, a significant improvement is observed.

EXAMPLE 8

An insoluble tablet is prepared by mixing the following substances:

| | |
|---|---|
| compound of formula (III) | 0.025 g |
| Lactose | 0.082 g |
| Stearic acid | 0.003 g |
| Talc, purified | 0.015 g |
| Sweetener qs | |
| Colourings qs | |
| Rice starch qs | 0.500 g |

Three tablets a day are administered orally to an individual suffering from psoriasis. After 30 days of treatment on the basis of 1 mg per kg of body weight of the subject being treated and per day, a significant improvement is observed.

EXAMPLE 9

A two-part anti-acne kit is produced:

| a) a gel having the following formulation is prepared: | |
|---|---|
| Ethyl alcohol | 48.70 g |
| Propylene glycol | 50.00 g |
| Crosslinked polyacrylic acid sold by the company "GOODRICH" under the name "CARBOPOL 940" | 1.00 g |
| Butylated hydroxyanisole | 0.05 g |
| Butylated hydroxytoluene | 0.05 g |
| α-Tocopherol | 0.10 g |
| compound of formula (IV) | 0.10 g |
| b) a gel having the following formulation is prepared: | |
| Ethyl alcohol | 5.00 g |
| Propylene glycol | 5.00 g |
| Ethylenediaminetetraacetic acid disodium salt | 0.05 g |
| Crosslinked polyacrylic acid sold by the company "GOODRICH" under the name "CARBOPOL 940" | 1.00 g |
| Triethanolamine (99%) | 1.00 g |

-continued

| | |
|---|---|
| Sodium lauryl sulphate | 0.10 g |
| Water, purified | 75.05 g |
| Benzoyl peroxide, water content 25% | 12.80 g |

Equal weights of the two gels are mixed at the required time immediately before use.

This mixture is applied twice a day to skin affected by acne. After 4 to 6 weeks of treatment on the basis of 2 to 10 mg per cm² of skin treated and per application, a significant improvement is observed.

We claim:

1. A process for preparing a stereospecific retinoid having the formula

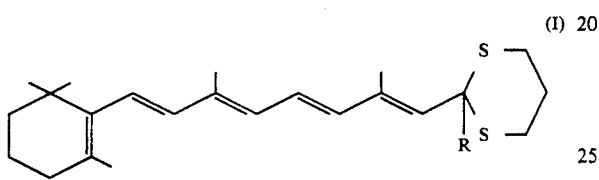
(I)

wherein R is H or a $C_1$-$C_4$ thioalkyl radical, said process comprising reacting a dithianepropenol having the formula

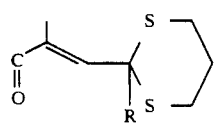
(VI)

wherein R has the meaning given above with ethynyl-β-ionol having the formula

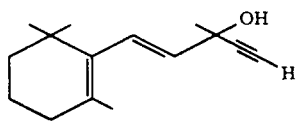
(VII)

in the presence of an organomagnesium compound, so as to obtain an acetylenic compound having the formula

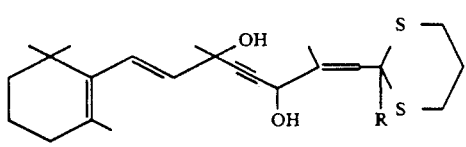
(VIII)

wherein R has the meaning given above, hydrogenating the acetylenic bond of the compound of formula VIII so as to obtain a diol having the formula

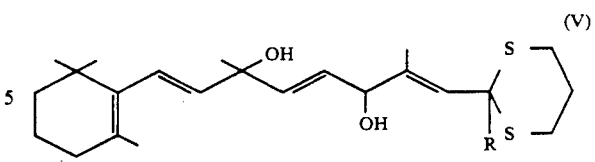
(V)

wherein R has the meaning given above and reducing said diol of formula V using a "low-valency" titanium.

2. The process of claim 1 wherein the hydrogenation of the compound of formula VIII is performed using lithium aluminum hydride.

3. A process for the treatment of acne or psoriasis comprising administering to a person suffering from acne or psoriasis, at a daily dosage of approximately 0.01 mg to approximately 100 mg/kg of body weight, in 1 to 3 doses, a stereospecific retinoic derivative having the formula

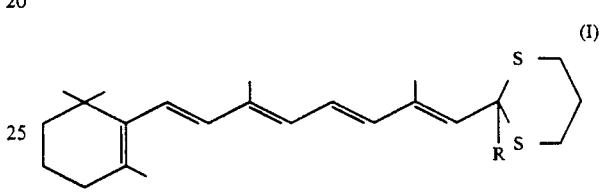
(I)

wherein R is H or a $C_1$-$C_4$ thioalkyl radical.

4. A pharmaceutical composition for the treatment of acne or psoriasis comprising in a pharmaceutically acceptable carrier a stereospecific retinoic derivative having the formula

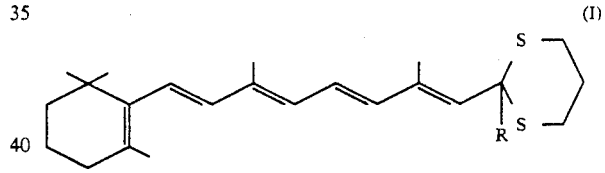
(I)

wherein R is H or a $C_1$-$C_4$ thioalkyl radical, said retinoic derivative being present in an amount ranging from 0.0001 to approximately 5 percent by weight based on the total weight of said composition.

5. A cosmetic composition for body and hair hygiene comprising in a cosmetically acceptable carrier a stereospecific retinoic derivative having the formula

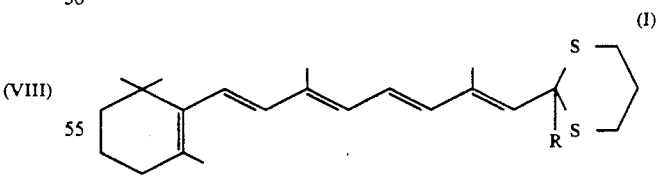
(I)

wherein R is H or a $C_1$-$C_4$ thioalkyl radical, said retinoic derivative being present in an amount ranging from 0.0001 to approximately 3 percent by weight based on the total weight of said composition.

* * * * *